US011583543B2

(12) United States Patent
Anderson

(10) Patent No.: US 11,583,543 B2
(45) Date of Patent: Feb. 21, 2023

(54) AMBROXOL TO IMPROVE AND/OR EXTEND HEALTHSPAN, LIFESPAN AND/OR MENTAL ACUITY

(71) Applicant: NeueRe, LLC, Princeton, NJ (US)

(72) Inventor: Stephen Anderson, Princeton, NJ (US)

(73) Assignee: NeueRe, LLC, Princeton, NJ (US)

( * ) Notice: Subject to any disclaimer, the term of this patent is extended or adjusted under 35 U.S.C. 154(b) by 0 days.

(21) Appl. No.: 16/631,266

(22) PCT Filed: Jul. 14, 2018

(86) PCT No.: PCT/US2018/042193
§ 371 (c)(1),
(2) Date: Jan. 15, 2020

(87) PCT Pub. No.: WO2019/018247
PCT Pub. Date: Jan. 24, 2019

(65) Prior Publication Data
US 2020/0215089 A1    Jul. 9, 2020

Related U.S. Application Data

(60) Provisional application No. 62/574,848, filed on Oct. 20, 2017, provisional application No. 62/533,071, filed on Jul. 16, 2017.

(51) Int. Cl.
*A61K 31/7036* (2006.01)
*A61P 39/00* (2006.01)
*A61K 31/136* (2006.01)

(52) U.S. Cl.
CPC ........ *A61K 31/7036* (2013.01); *A61K 31/136* (2013.01); *A61P 39/00* (2018.01)

(58) Field of Classification Search
CPC .... A61K 31/7036; A61K 31/136; A61P 39/00
USPC ........................................................ 514/42
See application file for complete search history.

(56) References Cited

U.S. PATENT DOCUMENTS

| 10,894,008 B2 * | 1/2021 | Anderson ............... A61P 17/04 |
| 2005/0266058 A1 | 12/2005 | Esperester et al. |
| 2013/0096142 A1 | 4/2013 | Topol et al. |
| 2014/0161916 A1 | 6/2014 | Khusial et al. |
| 2016/0000737 A1 * | 1/2016 | Zemel .................... A61K 36/61 424/442 |
| 2018/0296464 A1 | 10/2018 | Graban et al. |
| 2018/0353397 A1 | 12/2018 | Park et al. |

FOREIGN PATENT DOCUMENTS

| CA | 2565183 A1 | 11/2005 |
| WO | 2008021829 A3 | 10/2008 |
| WO | 2019018247 A1 | 1/2019 |

OTHER PUBLICATIONS

Haque et al. Effect of Ambroxol, Spirulina and Vitamin-E in Naphthalene Induced Cataract in Female Rats. Indian J Physiol Pharmacol 2005; 49 (1) : 57-64. (Year: 2005).*
Migdalska-Richards et al. Oral ambroxol increases brain glucocerebrosidase activity in a nonhuman primate. Synapse. 2017;71: e21967. https://doi.org/10.1002/syn.21967 (Year: 2017).*
"MIT Technology Review—Old Age is Over! If You Want it", MIT Technology Review, vol. 122, No. 5 The Longevity Issue, (2019).
Abd et al., "Skin Models for the Testing of Transdermal Drugs", Clinical Pharmacology: Advances and Applications, vol. 8, pp. 163-176, (2016).
Agner et al., "Quantification of the DMSO-Response—a Test for Assessment of Sensitive Skin", Clinical and Experimental Dermatology, vol. 14, pp. 214-217, (1989).
Antonov et al.,"Methods for the Assessment of Barrier Function", Curr Probl Dermatol. Basel, vol. 49, pp. 61-70, (2016).
Bank of America Merrill Lynch, "Cosmetics, Household & Personal Care Industy Primer", Cosmetics, Household & Personal Care, pp. 1-191, (2017).
Breiden et al., "The Role of Sphingolipid Metabolism in Cutaneous Permeability Barrier Formation", Biochimica et Biophysica Acta, vol. 1841, pp. 441-452, (2014).
Cabasso et al., "*Drosophila melanogaster* Mutated in its GBA1b Ortholog Recapitulates Neuronopathic Gaucher Disease", J. Clin. Med, vol. 8, No. 1420, pp. 1-23, (2019).
Chauhan et al., "Pharmaceutical Screen Identifies Novel Target Processes for Activation of Autophagy with a Broad Translational Potential", Nature Communications, vol. 6, No. 1, pp. 1-15, (2015).
Chesselet and Anderson, "Final Report: Testing of Ambroxol in the Thy1-αSyn Mouse Model of PD", Presentation for the Michael J. Fox Foundation, date of publication on the internet: Feb. 6, 2017.
Choi et al., "Ambroxol Induces Autophagy and Potentiates Rifampin Antimycobacterial Activity", Antimicrobial Agents and Chemotherapy, vol. 62, Issue 9, pp. 1-5, (2018).
Choi et al., "Autophagy in Human Health and Disease", N Engl J Med, vol. 368, pp. 651-662, (2013).
Efeyan et al., "Nutrient Sensing Mechanisms and Pathways", Nature, vol. 517, pp. 302-310, (2015 ).
Farwick et al., "Developments in Ceraminde Identification, Synthesis, Function and Nomenclature", Cosmetics & Toiletries, vol. 124, No. 2, pp. 63-72, (2009).
Feingold et al., "Role of Lipids in the Formation and Maintenance of the Cutaneous Permeability Barrier", Biochimica et Biophysica Acta, vol. 1841, pp. 280-294, (2014).
Fluhr et al., "Transepidermal Water Loss Reflects Permeability Barrier Status: Validation in Human and Rodent In Vivo and Ex Vivo Models", Experimental Dermatology, vol. 15, pp. 483-492, (2006).
Galluzzi et al., "Pharmacological Modulation of Autophagy: Therapeutic Potential and Persisting Obstacles", Nature Reviews, vol. 16, pp. 487-511, (2017).

(Continued)

*Primary Examiner* — Yih-Horng Shiao
(74) *Attorney, Agent, or Firm* — Michele M. Wales; InHouse Patent Counsel, LLC

(57) ABSTRACT

Compositions and methods for extending life expectancy are described herein. Specifically, ambroxol, ambroxol hydrochloride, and/or bromhexine can be used in a method for (a) treating, inhibiting, or reducing aging of a subject, (b) treating, inhibiting, or reducing an age-related symptom or an age-related disease in a subject, and/or (c) increasing the healthspan, lifespan, and/or mental acuity of a subject.

18 Claims, 3 Drawing Sheets

(56) References Cited

OTHER PUBLICATIONS

Granger et al., "Is Aging as Inevitable as Death and Taxes?", Cell Metabolism, vol. 23, pp. 947-948, (2016).
Hall et al., "A Trial for the Ages", Science, vol. 349, Issue 6254, pp. 1274-1278, (2015).
Holleran et al., "Consequences of β-Glucocerebrosidase Deficiency in Epidermis", The Journal of Clinical Investigation, Inc., vol. 93, pp. 1756-1764, (1994).
International Search Report and Written Opinion dated Apr. 25, 2019 and received in PCT/US2019/015137.
Kern K-U et al., "Topical Ambroxol for the Treatment of Neuropathic Pain", Schmerz, Der, Springer Verlag, Berlin, DE, vol. 29, No. 3, pp. S89-S96, (2015).
Lapierre et al., "Transcriptional and Epigenetic Regulation of Autophagy in Aging", Autophagy, vol. 11, No. 6, pp. 867-880, (2015).
Leslie et al., "A Putative Antiaging DrugTakes a Step From Mice to Men", Science, vol. 342, pp. 789, (2013).
Lim et al., "Aquatide Activation of SIRT1 Reduces Cellular Senescence Through a SIRT1-FOXO1-Autophagy Axis", Biomol Ther, vol. 25, No. 5, pp. 511-518, (2017).
Lopez et al., "The Hallmarks of Aging", Cell, vol. 153, pp. 1194-1217, (2013).
McNeill et al., "Ambroxol Improves Lysosomal Biochemistry in Glucocerebrosidase Mutation-Linked Parkinson Disease Cells", Brain, pp. 1-15, (2014).
Meckfessel et al.,"The Structure, Function, and Importance of Ceramides in Skin and Their Use as Therapeutic Agents in Skin-Care Products", J Am Acad Dermatol, vol. 71, No. 1, pp. 177-184, (2014).
Migdalska-Richards et al., "Ambroxol Effects in Glucocerebrosidase and a-Synuclein Transgenic Mice", Magazine, pp. 766-775, (2016).
Monzon et al., "Ambroxol-lnduced Systemic Contact Dermatitis Confirmed by Positive Patch Test", Research Letters, pp. 167-168, Document downloaded from http://www.elsevier.es, on Oct. 10, 2017.
Moors et al., "Therapeutic Potential of Autophagyenhancing Agents in Parkinson's Disease", Molecular Neurodegeneration, vol. 12, No. 11, pp. 1-18, (2017).
Nasto et al., "Biotech at the Beauty Counter", Nature Biotechnology, vol. 25, No. 6, pp. 617-619, (2007).
Notman et al., "The Permeability Enhancing Mechanism of DMSO in Ceramide Bilayers Simulated by Molecular Dynamics", Biophysical Journal, vol. 93, pp. 2056-2068, (2007).
Numan et al., "Ambroxol Hydrochloride, a Chaperone Therapy for Paget's Disease of Bone and Other Common Autophagy-Mediated Aging Diseases?", Integrative Clinical Medicine, vol. 1, No. 2, pp. 1-2, (2017).
Olshansky et al., "Measuring our Narrow Strip of Life", Nature , vol. 538, pp. 175-176, (2016).
Orourke et al., "MXL-3 and HLH-30 Transcriptionally Link Lipolysis and Autophagy to Nutrient Availability", Nat Cell Biol., vol. 15, No. 6, pp. 668-676, (2013).
Partridge et al., "Leading Edge Voices: Focus on Aging", Cell Metabolism, pp. 951-956, (2016).
Perera-Zoncu et al., "The Lysosome as a Regulatory Hub", Annu. Rev. Cell Dev. Biol., vol. 32, pp. 223-253, (2016).
Rinaldi et al., "Healing Beauty?", European Molecular Biology Organization, vol. 9, No. 11, pp. 1073-1077, (2008).
Shim et al., "A Protein Restriction-Dependent Sulfur Code for Longevity", Cell, vol. 160, pp. 15-17, (2015).
Van Sweden et al., "LC/WS Analysis of Stratum Corneum Lipids: Ceramide Profiling and Discovery", Journal of Lipid Research, vol. 52, pp. 1211-1221, (2011).
Van Sweden et al., "Combined LC/WS-Platform for Analysis of All Wajor Stratum Corneum Lipids, and the Profiling ol Skin Substitutes", Biochimica et Biophysica Acta, vol. 1841, pp. 70-79, (2014).
Ye et al., "Topical Applications of an Emollient Reduce Circulating Pro-Inflammatory Cytokine Levels in Chronically Aged Humans: a Pilot Clinical Study", European Academy of Dermatology and Venereology, pp. 1-7, (2019).
International Search Report and Written Opinion dated Dec. 3, 2018 and received in PCT/US2018/042193.
Magalhaes et al., "Effects of Ambroxol on the Autophagy-Lysosome Pathway and Mitochondria in Primary Cortical Neurons", Scientific Reports, vol. 8, No. 1385, pp. 1-12, (2018).
Partial Written Opinion and International Search Report dated Oct. 9, 2018 in PCT/US2018/042193.
Tai et al., "Autophagy Impairment with Lysosomal and Mitochondrial Dysfunction is an Important Characteristic of Oxidative Stress-Induced Senescence", Autophagy, vol. 13, No. 1, pp. 99-113, (2016).

* cited by examiner

AMBROXOL TO IMPROVE AND/OR EXTEND HEALTHSPAN, LIFESPAN AND/OR MENTAL ACUITY

CROSS-REFERENCE TO RELATED APPLICATIONS

This application is a § 371 National Stage Application of PCT/US18/42193 filed on Jul. 14, 2018, which claims priority to U.S. Ser. No. 62/533,071 filed on Jul. 16, 2017 and U.S. Ser. No. 62/574,848 filed on Oct. 20, 2017. These documents are hereby incorporated by reference in their entirety.

BACKGROUND OF THE INVENTION

Field of the Invention

The invention relates to the use of ambroxol, ambroxol hydrochloride, and/or bromhexine to improve and/or extend healthspan, lifespan, and/or mental acuity in a subject. The invention further relates to inhibiting and/or reducing the aging process, including the reduction of symptoms associated with aging by using ambroxol, ambroxol hydrochloride, and/or bromhexine.

Discussion of the Related Art

Growing evidence supports the linkage of metabolism and the aging process. Compared to ad libitum feeding, dietary restriction (DR) or calorie restriction (CR) consistently has been shown to extend lifespan and delay age-related diseases in evolutionarily diverse organisms. However, researchers still search for a "pill" that can mimic these results of dietary restriction to reduce the aging process without requiring diet changes.

For example, the number of people aged 60 years and over has tripled since 1950, reaching 600 million in 2000 and surpassing 700 million in 2006. Furthermore, it is projected that the combined senior and geriatric population will reach 2.1 billion by 2050. With increased chronological age, progressive aging of organ systems also occurs. As a consequence, aged individuals have a dramatically increased risk of numerous debilitating diseases including bone fractures, cardiovascular disease, cognitive impairment, diabetes and cancer, leading to difficulty for the patient's well-being as well as stressing the health care system. Therefore, identifying ways to prevent or delay age-associated frailty and diseases is imperative for maintaining the health of our population as well as our nation's economy.

Thus, need exists for a non-dietary based method of treatment for age-related symptoms and age-related diseases, such diseases including but not limited to cancer, diabetes, and cardiovascular disease thereby extending the healthspan, lifespan, and/or mental acuity of subjects.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention relates to compositions and methods for extending life expectancy. Specifically, ambroxol, ambroxol hydrochloride, and/or bromhexine can be used in a method for (a) treating, inhibiting, or reducing aging of a subject, (b) treating, inhibiting, or reducing an age-related symptom or an age-related disease in a subject, and/or (c) increasing the healthspan, lifespan, and/or mental acuity of a subject.

Specifically, the invention relates to a method of prolonging healthspan, lifespan, and/or mental acuity of a subject, comprising administering to the subject an effective amount of ambroxol, ambroxol hydrochloride, and/or bromhexine. The invention also relates to ambroxol, ambroxol hydrochloride, and/or bromhexine, as a medicament for extending life expectancy and/or reducing aging or an age-related illness. The invention also relates to a composition for the treatment of extending life expectancy comprising a therapeutically effective amount of ambroxol, ambroxol hydrochloride, and/or bromhexine, together with a pharmaceutically acceptable excipient.

In some embodiments, enantiomers, analogs, esters, amides, prodrugs, or metabolites of ambroxol and/or bromhexine, or a salt of ambroxol or bromhexine, particularly a pharmaceutically acceptable salt can be used. In preferred embodiments, bromhexine or a salt of bromhexine is used. In some embodiments, the salt of ambroxol or bromhexine is a hydrochloride.

Thus, the invention relates to a method for increasing, promoting and/or improving lifespan, healthspan (e.g., healthy aging) and/or mental acuity in a subject, wherein said method comprises administering to the subject a therapeutically effective amount of ambroxol, ambroxol hydrochloride, and/or bromhexine. The invention further relates to treating, inhibiting, and/or reducing aging, an age-related symptom, and/or an age-related disease in the subject, wherein said method comprises administering to the subject a therapeutically effective amount of ambroxol, ambroxol hydrochloride, and/or bromhexine.

Examples of age-related symptoms and/or age-related diseases include, but are not limited to cardiovascular disease, a metabolic syndrome, a bone-loss disorder, a neurodegenerative disease, pre-diabetes, diabetes, obesity, osteoporosis, coronary artery disease, cerebrovascular disease, heart attack, stroke, peripheral arterial disease, aortic valve disease, stroke, mild cognitive impairment, pre-dementia, dementia, macular degeneration, and cataracts, hair thinning, hair graying, loss of mobility, loss of stamina, fatigue, increased susceptibility to infection, a metabolic change, a biochemical change, cardiac hypertrophy, heart failure, myocardial infarction, ischemia reperfusion injury, inflammatory disease, proinflammatory states, arthropathies, autoimmune diseases, and/or Alzheimer's Disease.

For example, a daily dosage from about 20-500 mg/day, 50-150 mg/day, 50-200 mg/day, 50-250 mg/day, 250-500 mg/day, or 250 mg-1000 mg/day may be utilized. Higher or lower doses are also contemplated as it may be necessary to use dosages outside these ranges in some cases. The daily dosage may be divided, such as being divided equally into two to four times per day daily dosing.

As described below, in a mouse model, it was unexpectedly found that the doses of ambroxol that improved age related symptoms were substantially lower than doses previously observed to effectively promote GCase chaperoning activity in the mouse. Thus, in preferred embodiments, long-term administration of ambroxol, bromhexine, or a salt thereof administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, or between 50-150 mg/day, 50-200 mg/day, 50-250 mg/day, 250-500 mg/day, or 250 mg-1000 mg/day, or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day is expected to be effective in improving healthspan, lifespan, and/or mental acuity.

In further embodiments, the invention includes a long-term method of inducing increasing and/or improving healthspan, lifespan, and/or mental acuity of a subject the method comprising administering a therapeutically effective amount of ambroxol, ambroxol hydrochloride, and/or bromhexine, wherein the administration of the compound is at least for 1, 2, 3, 4, 5, 6, 7, 8, 9, or 10 years.

In further preferred embodiments, the lifespan, healthspan, mental acuity and/or healthy aging of the subject is extended, improved, or promoted by up to about 10%, 20%, 30%, 40%, 50%, 60%, or 70% as compared to untreated control subjects. In further preferred embodiments, the aging, the age-related symptoms, and/or the age-related diseases are treated, inhibited, and/or reduced in the subject by up to about 10%, 20%, 30%, 40%, 50%, 60%, or 70% as compared to untreated control subjects.

In preferred embodiments, the subject is a mammal, and even in further preferred embodiments, the mammal is a human, a domesticated animal (e.g., a dog, a cat, a horse) or a farm animal (e.g., a cow or a pig).

BRIEF DESCRIPTION OF THE FIGURES

The objects and features of the invention can be better understood with reference to the following detailed description and accompanying drawings.

DETAILED DESCRIPTION

I. Definitions

Figure 1:
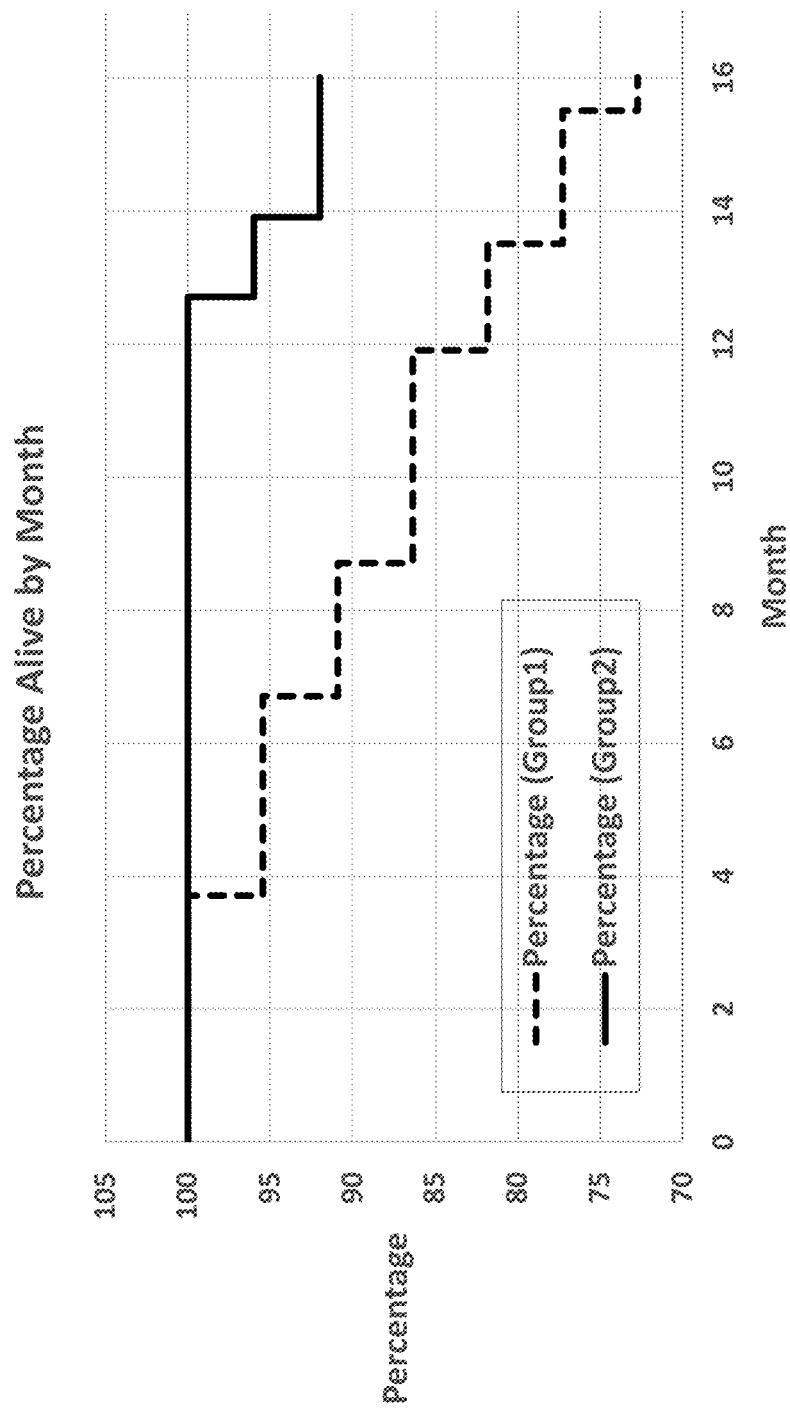
FIG. 1 provides animal data showing that ambroxol was able to increase lifespan in a mouse animal model. Group 1 represents control animals that were not administered ambroxol; Group 2 represents animals administered 50 mg/kg (body weight) of ambroxol daily as a chow supplement, starting at 2 months of age FIG. 2. Mice were tested at age 7 months for novel place recognition. This is a cognitive test to measure short term working memory, involving recognition of a familiar object found in an unfamiliar place (see Magen et al (2012) *Eur. J. Neurosci.* 35: 870-882; Magen and Chesselet (2011) *J. Parkinson's Disease* 1: 217-227). A Discrimination Index (DI)=$(t_{novel}-t_{familiar})/(t_{novel}+t_{familiar})$ is used to assess the time spent exploring near the object in a novel place ("$t_{novel}$") vs. the total exploration time overall. Discrimination Index scores greater than zero are considered to indicate good place recognition memory.
Figure 2:
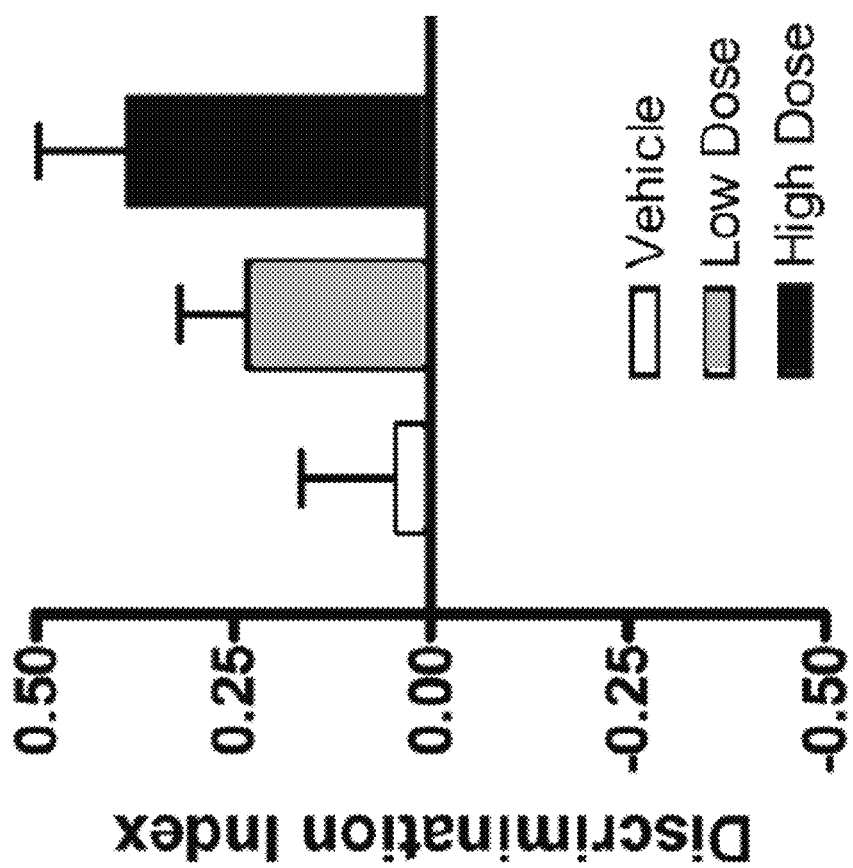

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

As used herein, a "subject" is a vertebrate, preferably a mammal, more preferably a human, and even more preferably a domesticated animal, such as a pet, or a farm animal. Mammals include, but are not limited to, murines, simians, humans, farm animals, sport animals, and pets. In other preferred embodiments, the "subject" is a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), or an ape (e.g., gorilla, chimpanzee, orangutan, gibbon). In other embodiments, non-human mammals, especially mammals that are conventionally used as models for demonstrating therapeutic efficacy in humans (e.g., murine, primate, porcine, canine, or rabbit animals) may be employed. In preferred embodiments, an "individual" or "patient" (as in the subject of the treatment) means mammals, particularly non-human primates, e.g. apes and monkeys, and most particularly humans. In preferred embodiments, subjects who are specifically excluded from the scope of the invention include humans suffering from a disease and/or humans (when the disease has a genetic basis) who are carriers of recessive alleles for the disease, wherein the disease is selected from a neurogenerative disease, such as, for example, Gaucher's Disease, parkinsonism (including Parkinson's Disease and Dementia with Lewy Bodies), Lysosomal Storage Disorders, Alzhemier's Disease, and/or Pick's disease.

As understood herein, an "effective amount" of a pharmaceutical composition of the instant invention refers to an amount of the composition suitable to elicit a therapeutically beneficial response in the subject, e.g., extend and/or increase and/or improve healthspan, lifespan, and/or mental acuity, such as for example, increasing survival and/or healthy aging and/or to decrease morbidity or age-related illness in the subject.

The term "dose" or "dosage" as used herein refers to physically discrete units suitable for administration to a subject, each dosage containing a predetermined quantity of the active pharmaceutical ingredient calculated to produce a desired response.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2 fold, of a value. Unless otherwise stated, the term 'about' means within an acceptable error range for the particular value, such as ±1-20%, preferably ±1-10% and more preferably ±1-5%. In even further embodiments, "about" should be understood to mean+/−5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All percentages and ratios used herein are by weight of the total composition unless otherwise indicated herein. All temperatures are in degrees Celsius unless specified otherwise. All measurements made are at 25° C. and normal pressure unless otherwise designated.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination.

The term "isolated compound" means a compound substantially free of contaminants or cell components with which the compound naturally occurs, or the reagents used in synthesis or the byproducts of synthesis. "Isolated" and "substantially free of contaminants" does not mean that the preparation is technically pure (homogeneous), but it is sufficiently pure to provide the compound in a form in which it can be used therapeutically.

A "derivative" compound, as the term is used herein, refers to a second compound that is derived from a first compound, such as a brominated version of a non-brominated parent compound. For example, ambroxol is a derivative of bromhexine.

As used herein, "lifespan" means the time until death.

As used herein "healthspan" or "healthy aging" means the time of life living free (or optimally free) of serious disease.

As used herein, "mental acuity" is a measure of a subject's cognitive abilities, such as ability to focus, attention span, and sharpness.

As used herein, "nutrient sensing" is a cell's ability to sense and respond to fluctuations in nutrient levels as is described in Efeyan et al., "Nutrient Sensing Mechanisms and Pathways," Nature 517: 302-310 (2015) (hereby incorporated by reference in its entirety).

As used herein "treating, inhibiting, and/or reducing aging, an age-related symptom, and/or an age-related disease" or the like means reducing the risk of occurrence, delaying the onset, slowing the progression, and/or reducing the severity and/or manifestation, of a sign of aging and/or degenerative disorder, and includes, but is not limited to, preventing the occurrence, development or progression of a sign of aging and/or degenerative disorder.

Compounds of the Invention

Ambroxol, ambroxol hydrochloride, and/or bromhexine can be used as described herein. Table 1 shows the structures of these compounds. These compounds may be used to provide a long-term treatment of a subject to increase healthspan, lifespan, and/or mental acuity, such as by prolonging survival and/or reducing morbidity and/or age-related illnesses.

Ambroxol, also known by its chemical name trans-4-(2-amino-3,5-dibromobenzylamino) cyclohexanol, has the structure as shown in Table 1. An aspect of the invention also includes a medicament to increase and/or improve healthspan, lifespan, and/or mental acuity, comprising a pharmaceutically acceptable salt of ambroxol. In one embodiment, the salt is a hydrochloride salt. Bromhexine, also known by its chemical name 2-amino-3,5-dibromo-N-cyclohexyl-N-methylbenzenemethanamine, has the structure as shown in Table 1. Thus, another aspect of the invention also includes a medicament to increase and/or improve healthspan, lifespan, and/or mental acuity, comprising a pharmaceutically acceptable salt of bromhexine. In one embodiment, the salt is a hydrochloride salt. Another aspect of the invention includes a pharmaceutically acceptable salt of a ambroxol and/or bromhexine.

TABLE 1

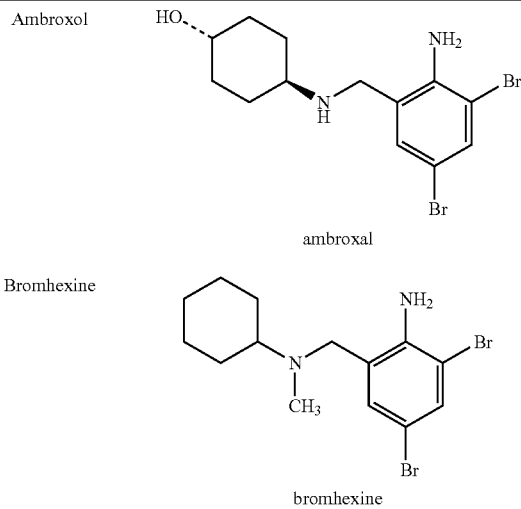

TABLE 1-continued

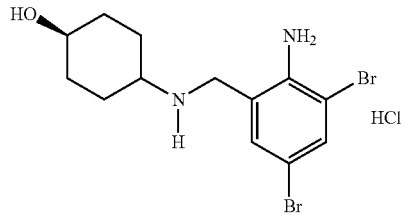

Ambroxol Hydrochloride

Preparation of Compounds of the Invention

The compounds of the invention are known and may be prepared by methods known to the person skilled in the art of organic synthesis. For example, U.S. Patent Application publication number US2004/0242700, incorporated herein by reference in its entirety, provides a synthetic protocol for the preparation of ambroxol.

Salts of Compounds of the Invention

For compounds that typically contain acidic or basic groups (such as carboxyl or amino groups) such groups will not necessarily be in the free base form. When referring to compounds of the invention, the reference is intended to include salt forms of the compound. Within the scope of the invention, therefore, are salts of the active agent, especially salts of ambroxol and bromhexine. The preferred salts are pharmaceutically-acceptable salts. Also within the scope of the invention are salts of derivatives of ambroxol.

The term "salts" embraces addition salts of free acids or free bases. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of therapeutic compounds.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and salfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, oxalic, malonic and galacturonic acid. Examples of pharmaceutically unacceptable acid addition salts include, for example, perchlorates and tetrafluoroborates. All of these acid addition salts may be prepared from ambroxol or bromhexine by reacting, for example, the appropriate acid with the compound.

Suitable pharmaceutically acceptable base addition salts of ambroxol or bromhexine include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, m eglumine(N-methyl glucamine) and procaine. Examples of pharmaceutically unacceptable base addition salts include lithium salts and cyanate salts. All of these base addition salts may be prepared from ambroxol or bromhexine by reacting, for example, the appropriate base with the compound.

Pharmaceutical Compositions

In an aspect, the invention includes a composition comprising a therapeutically effective amount of ambroxol or bromhexine or a pharmaceutically acceptable salt thereof, in conjunction with a pharmaceutically acceptable excipient for treatment of an individual to increase and/or improve healthspan, lifespan, and/or mental acuity, and/or to treat, inhibit, and/or reduce aging, age-related symptoms, and/or the age-related diseases. In another aspect, the invention includes a composition comprising a therapeutically effective amount of ambroxol or bromhexine or pharmaceutically acceptable salts thereof in conjunction with a pharmaceutically acceptable excipient to increase and/or improve healthspan, lifespan, and/or mental acuity, and/or to treat, inhibit, and/or reduce aging, age-related symptoms, and/or the age-related diseases in an individual. In another aspect, the invention includes a composition comprising a therapeutically effective amount of a derivative of ambroxol, including, but not limited to an enantiomer, analog, ester, amide, prodrug, or metabolite of ambroxol, or a pharmaceutically acceptable salt thereof, in conjunction with a pharmaceutically acceptable excipient for treatment of an individual to increase and/or improve healthspan, lifespan, and/or mental acuity, and/or to treat, inhibit, and/or reduce aging, age-related symptoms, and/or the age-related diseases.

The active agent (e.g., ambroxol or bromhexine or a pharmaceutically acceptable salt thereof) may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, tablets, capsules, solutions, parenteral solutions, troches, suppositories, or suspensions. For examples of the preparation of oral, topical, suppository and parenteral formulations of ambroxol, bromhexine, or other ambroxol derivatives, is disclosed in, for example, Examples 1-8 of WO2005/007146, or its equivalent US2005/00148747, incorporated herein by reference.

In another embodiment, ambroxol or bromhexine or a salt thereof is used in the preparation of a medicament to increase and/or improve healthspan, lifespan, and/or mental acuity, and/or to treat, inhibit, and/or reduce aging, age-related symptoms, and/or the age-related diseases.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol, or with a plant extract as a supplement. Solutions for parenteral administration preferably contain a water-soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents, absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 50 to about 1000 mg, more typically, about 250 to about 500 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

In further preferred embodiments, ambroxol or bromhexine or its salt thereof is administered as several doses over a given period of time, e.g., a daily dose for a week or more. For example, a daily dosage from about 20-500 mg/day, 50-150 mg/day, 50-200 mg/day, 50-250 mg/day, 250-500 mg/day, or 250 mg-1000 mg/day may be utilized. Higher or lower doses are also contemplated as it may be necessary to use dosages outside these ranges in some cases. The daily dosage may be divided, such as being divided equally into two to four times per day daily dosing.

In mouse models, it was unexpectedly found that the doses of ambroxol that improved age related symptoms were substantially lower than doses previously observed to effectively promote GCase chaperoning activity. Thus, in preferred embodiments, long-term administration of ambroxol or bromhexine or a salt thereof administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, or between 50-150 mg/day, 50-200 mg/day, 50-250 mg/day, 250-500 mg/day, or 250 mg-1000 mg/day, or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day is expected to be effective in improving healthspan, lifespan, and/or mental acuity.

In further embodiments, the invention includes a long-term method of inducing increasing and/or improving healthspan, lifespan, and/or mental acuity of a subject, and/or to treat, inhibit, and/or reduce aging, age-related symptoms, and/or the age-related diseases, preferably in a human, the method comprising administering a therapeutically effective amount of ambroxol, bromhexine, or a salt thereof, wherein the administration of the compound is at least for 1, 2, 3, 4, 5, 6, 7, 8, 9, or 10 years.

In further preferred embodiments, the lifespan, healthspan, mental acuity and/or healthy aging of the subject is extended, improved, or promoted by up to about 10%, 20%, 30%, 40%, 50%, 60%, or 70% as compared to untreated control subjects. In further preferred embodiments, the aging, the age-related symptoms, and/or the age-related diseases are treated, inhibited, and/or reduced in the subject by up to about 10%, 20%, 30%, 40%, 50%, 60%, or 70% as compared to untreated control subjects.

The pharmaceutical compositions of the present invention may also be formulated so as to provide slow or controlled release of the active ingredient therein using, for example, hydropropylmethylcellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation may comprise the compound of the invention, propylene glycol, sterile water, ethanol and sodium chloride. Alternative solvents which may be used instead of propylene glycol include glycerol and polyethylene glycol. Capsules, blisters and cartridges (made, for example, from gelatin or HPMC) for use in an inhaler or insufflator may be formulated to contain a powder mix of ambroxol or bromhexine or a pharmaceutically acceptable salt thereof, a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted- and programmed-release formulations. Sustained or controlled release can be obtained by using, for example, poly(D,L-lactic-co-glycolic acid).

Administration of Compounds of the Invention

In a preferred embodiment, the compounds of the invention are administered orally to a patient. However, the compounds may be administered by any route, including by rectal, pulmonary, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration.

The dosing interval may be once a week, twice a week, every-other-day, once per day, typically once, twice, three times or four times per day with the doses given at equal intervals throughout the day and night in order to maintain a constant presence of the drug. However, the skilled artisan will be aware that a treatment schedule can be optimized for any given patient, and that administration of compound may occur less frequently than once per day. The treatment may be carried out for as long a period as necessary.

The specific dose of a compound according to the invention to obtain therapeutic benefit to increase and/or improve healthspan, lifespan, and/or mental acuity, and/or to treat, inhibit, and/or reduce aging, age-related symptoms, and/or the age-related diseases will, of course, be determined by the particular circumstances of the individual patient including the size, weight, age and sex of the patient, and the route of administration of the compound.

For example, a daily dosage from about 20-500 mg/day, 50-150 mg/day, 50-200 mg/day, 50-250 mg/day, 250-500 mg/day, or 250 mg-1000 mg/day may be utilized. Higher or lower doses are also contemplated as it may be necessary to use dosages outside these ranges in some cases. The daily dosage may be divided, such as being divided equally into two to four times per day daily dosing.

In mouse models, it was unexpectedly found that the predicted doses of ambroxol to improve age related symptoms as described herein occurred at doses substantially lower than doses previously observed to effectively promote GCase chaperoning activity. Thus, in preferred embodiments, long-term administration of ambroxol or bromhexine or a salt thereof administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day 1000 mg/day, 1050 mg/day, 1100 mg/day, 1150 mg/day, 1200 mg/day, or between 50-150 mg/day, 50-200 mg/day, 50-250 mg/day, 250-500 mg/day, or 250 mg-1000 mg/day, or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day is expected to be effective in improving healthspan, lifespan, and/or mental acuity.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

Without further description, it is believed that one of ordinary skill in the art can, using the preceding description and the following illustrative example, make and utilize the compounds of the present invention and practice the claimed methods. The following working example therefore, specifically points out the preferred embodiments of the present invention, and is not to be construed as limiting in any way the remainder of the disclosure. Although the invention herein has been described with reference to embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLE

The invention will now be further illustrated with reference to the following examples. It will be appreciated that what follows is by way of example only and that modifications to detail may be made while still falling within the scope of the invention.

Example 1: Animal Model Showing Ambroxol's Activity in Improving Lifespan

Weaned male BDF1 mice were raised from pups, housed 1-4 animals per cage and fed Teklad 7013 NIH-31 rodent chow and water ad libitum. At 2 months of age, the mice were divided into two roughly equal groups of 22-25 animals. One group continued to be fed the Teklad chow as before (control); the other group was switched to Teklad chow formulated with ambroxol at 300 mg per kg of chow. This formulation was designed, based on the average ad libitum chow consumption of an adult male BDF1 mouse, to deliver 50 mg/kg/day (based on body mass) to each mouse in the treated group. Mice were maintained on this diet until they died naturally or until they reached 16 months of age, at which time the experiment ended. During the course of the experiment all mice were periodically removed from their cages and handled in the course of subjecting them to various sensorimotor, cognitive, and/or behavioral tests.

FIG. 1 provides animal data showing that ambroxol was able to increase lifespan in a mouse animal model. Group 1 represents control animals that were not administered ambroxol; Group 2 represents animals administered 50 mg/kg of ambroxol daily as a chow supplement, starting at 2 months of age.

Preliminary data also suggests that not only did ambroxol increase lifespan, but that when sacrificed, surviving animals of Group 2 appeared at least as healthy, on average, as did the Group 1 animals, indicating that healthspan was extended in parallel with lifespan.

Example 2: Animal Model Showing Ambroxol's Activity in Improving Cognitive Function In this experiment, three groups of mice, with at least 13 mice in each group, were given a cognitive acuity test at 7 months. A dose-related improvement in cognitive acuity was observed, with the "High Dose" Group (150 mg/kg/day) showing the best cognitive acuity results, the "Low Dose" (50 mg/kg/day) Group showing results in between the Control Group and the "High Dose" Group of animals, and the Control Group (no ambroxol) showing the base line cognitive acuity results.

Moreover, these dosage results are unexpected and surprising as they are substantially lower than doses previously observed to effectively promote GCase chaperoning activity in mice. See, e.g., Migdalska-Richards et al (2016) *Ann. Neurol.* 80: 766-775.

Example 3: Ambroxol Induces Macroautophagy in Mouse Cells in Culture

Figure 3:
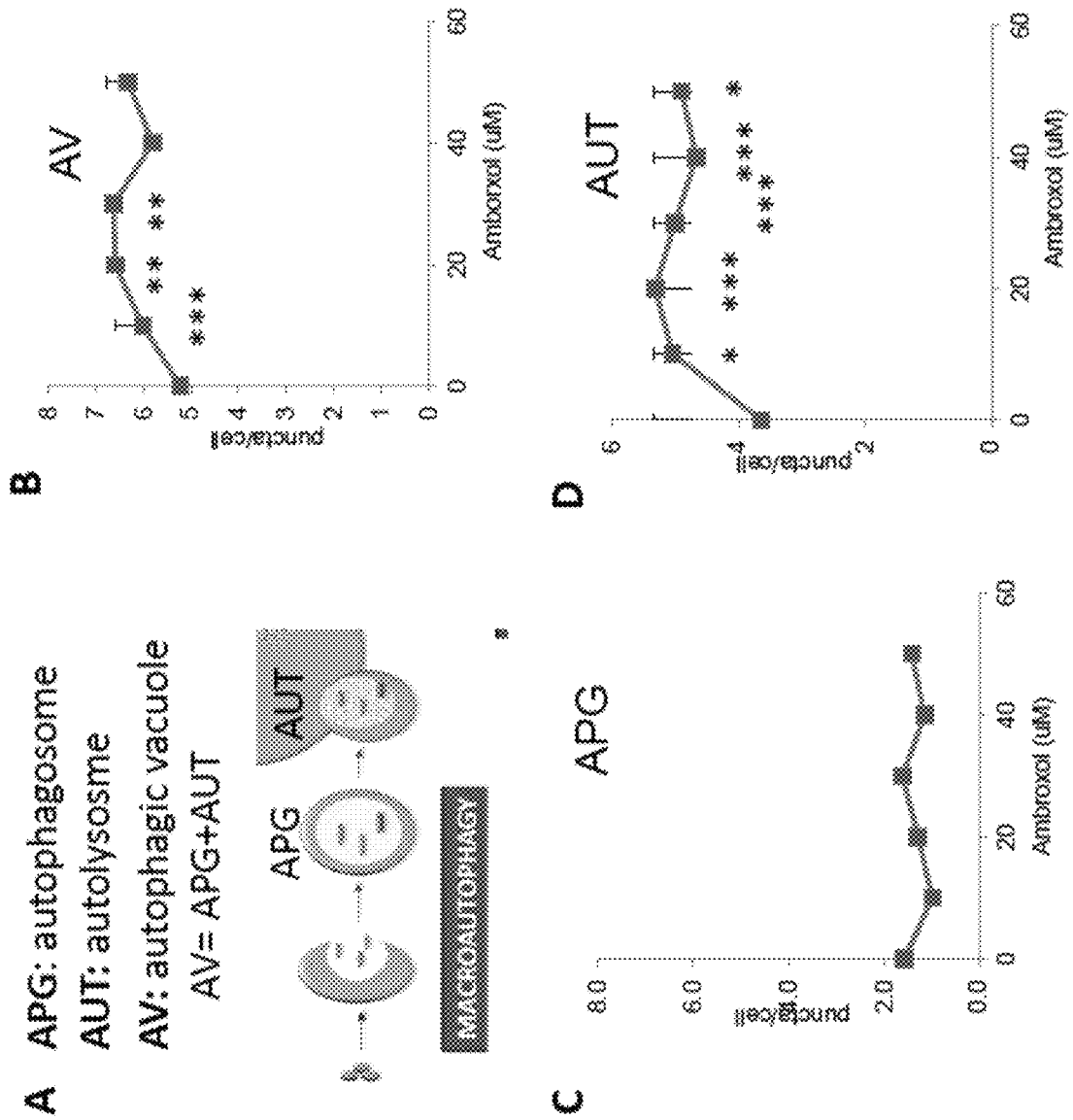
FIG. 3. Effect of Ambroxol on basal macroautophagy in mouse cells. Mouse fibroblasts in culture (NIH3T3 cells) expressing the tandem reporter mCherry-GFP-LC3 were exposed to the indicated concentrations of Ambroxol for 24 h in complete media. Panel A. Schematic of the autophagic compartments analyzed. Panels B-D. Number of autophagic vacuoles (AV) (Panel B); autophagosomes (APG) (Panel C); and autolysosomes (AUT) (Panel D). All values are mean+ s.e.m. and quantifications were done in at least 2,500 cells per condition in three different experiments using high content microscopy. Differences with untreated (0 uM ambroxol) are significant for *$p<0.05$ $p<0.01$ and *$p<0.001$.

FIG. 3 shows the effect of ambroxol on basal macroautophagy in mouse cells. Mouse fibroblasts (NIH3T3) were obtained from the American Type Culture Collection (ATCC). Cells were maintained in Dulbecco's modified Eagle's medium (DMEM) (Sigma, St. Louis, Mo.) in the presence of 10% newborn calf serum (NCS), 50 µg/ml penicillin, and 50 µg/ml streptomycin at 37° C. with 5% $CO_2$. Cells plated in glass-bottom 96-well plates were treated for the indicated time and after fixation images were acquired using a high-content microscope (Operetta, PerkinElmer). Images of 9 different fields per well were captured, resulting in an average of 2,500-3,000 cells. Nuclei and puncta were identified using the manufacturer's software. The number of particles/puncta per cell was quantified using the 'particle identifier' function in the cytosolic region after thresholding in non-saturated images. In all cases, focal plane thickness was set at 0.17 µm and sections with maximal nucleus diameter were selected for quantification. Values are presented as number of puncta per cell section that in acquisition conditions represents 10-20% of the total puncta per cell. Macroautophagy activity in intact cells was measured upon transduction with lentivirus carrying the mCherry-GFP-LC3 tandem construct. Kimura S., Noda. T, & Yoshimori T "*Dissection of the autophagosome maturation process by a novel reporter protein, tandem fluorescent-tagged LC3*," Autophagy 3(5):452-460 (2007). Cells were plated on glass-bottom 96 well plates and fluorescence was read in both channels. Puncta positive for both fluorophores correspond to autophagosomes, whereas those positive for only the red fluorophore correspond to autolysosomes. Autophagic flux was determined as the conversion of autophagosomes (yellow) to autolysosomes (red only puncta).

Without being bound by theory, ambroxol may, apart from its pharmacological activity as a GCase chaperone, be inhibiting nutrient sensing. By interfering with nutrient sensing, ambroxol may be triggering a response by the cells of the animal appropriate to the organism entering a nutrient-limited or fasting state, thus sending the organism into a "catabolic signaling" mode characterized by transcription factor EB (TFEB) dephosphorylation, CLEAR network transcription, lysosome biogenesis, and autophagy induction, leading to improved lifespan, healthspan and/or cognitive acuity. See, e.g., Efeyan et al., "*Nutrient Sensing Mechanisms and Pathways*," Nature 517: 302-310 (2015) (hereby incorporated by reference in its entirety). Thus, ambroxol, ambroxol hydrochloride, and/or bromhexine (including the low doses as described below), may systemically inhibit nutrient sensing resulting in the whole organism entering catabolic signaling mode.

The human equivalent doses (HEDs), calculated from the "low" and "high" mouse doses of this study, are approximately 4 mg/kg/day and 12 mg/kg/day, which is approximately 250 mg/day or 750 mg/day for an average 62.5 kg human. Thus, in preferred embodiments, long-term administration of ambroxol or bromhexine or a salt thereof administered at a dose of approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, 1200 mg/day, or between 50-150 mg/day, 50-200 mg/day, 50-250 mg/day, 250-500 mg/day, or 250 mg-1000 mg/day, or less than 1000 mg/day, or approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, 12 mg/kg/day, and/or between 4-12 mg/kg/day is expected to be effective in improving healthspan, lifespan, and/or mental acuity.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for increasing and/or improving lifespan in an animal, wherein said animal is selected from a canine, a feline, an equine, a non-human primate, a simian, an ape, a cow, or a pig, and wherein said method comprises administering to the animal a therapeutically effective amount of ambroxol or bromhexine or salt thereof, wherein the therapeutically effective amount to extend lifespan is obtained after monitoring percentage of animals alive for more than 1 year.

2. The method of claim 1, wherein said method reduces an age-related symptom or an age-related disease in the animal.

3. The method of claim 2, wherein the age-related symptom and the age-related disease is selected from a cardiovascular disease, a metabolic syndrome, a bone-loss disorder, a neurodegenerative disease, pre-diabetes, diabetes, obesity, osteoporosis, coronary artery disease, cerebrovascular disease, heart attack, stroke, peripheral arterial disease, aortic valve disease, stroke, mild cognitive impairment, pre-dementia, dementia, macular degeneration, cataracts, hair thinning, hair graying, loss of mobility, loss of stamina, fatigue, increased susceptibility to infection, a metabolic change, a biochemical change, cardiac hypertrophy, heart failure, myocardial infarction, ischemia reperfusion injury, inflammatory disease, proinflammatory states, arthropathies, autoimmune diseases, or Alzheimer's Disease.

4. The method of claim 1, wherein the ambroxol salt is ambroxol hydrocholoride.

5. The method of claim 1, wherein ambroxol or bromhexine or salt thereof is administered as several doses over a given period of time, selected from a daily dose for a week or more.

6. The method of claim 5, wherein ambroxol or bromhexine or salt thereof is administered as for at least 1, 2, 3, 4, 5, 6, 7, 8, 9, or 10 years.

7. The method of claim 1, wherein ambroxol or bromhexine or salt thereof is administered as a daily dose of about 20-500 mg/day, 50-150 mg/day, 50-200 mg/day, 50-250 mg/day, 250-500 mg/day, or 250 mg-1000 mg/day.

8. The method of claim 1, wherein ambroxol or bromhexine or salt thereof is administered as a daily dose selected from:
   (a) approximately 50 mg/day, 75 mg/day, 100 mg/day, 150 mg/day, 200 mg/day 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day, 1000 mg/day, 1050 mg/day, 1100 mg/day, 1150 mg/day, or 1200 mg/day;
   (b) 50-150 mg/day, 50-200 mg/day, 50-250 mg/day, 250-500 mg/day or 250 mg-1000 mg/day;
   (c) 20-1000 mg/day;
   (d) approximately 1 mg/kg/day, 2 mg/kg/day, 3 mg/kg/day, 4 mg/kg/day, 5 mg/kg/day, 6 mg/kg/day, 7 mg/kg/day, 8 mg/kg/day, 9 mg/kg/day, 10 mg/kg/day, 11 mg/kg/day, or 12 mg/kg/day; or
   (e) 4-12 mg/kg/day.

9. The method of claim 1, wherein the lifespan of the animal is extended by up to about 10%, 20%, 30%, 40%, 50%, 60%, or 70% as compared to untreated control animals.

10. The method of claim 1, wherein the animal is a pet.

11. The method of claim 1, wherein ambroxol or bromhexine or salt thereof inhibits nutrient sensing.

12. The method of claim 1, wherein ambroxol or bromhexine or salt thereof induces autophagy.

13. The method of claim 1, wherein said animal is selected from a dog, a cat, a horse, an ape, a marmoset, a baboon, a gorilla, a chimpanzee, an orangutan, or a gibbon.

14. The method of claim 1, wherein said animal is a cow.

15. The method of claim 1, wherein said animal is a pig.

16. The method of claim 1, wherein said animal is a cat.

17. The method of claim 1, wherein said animal is a dog.

18. The method of claim 1, wherein said animal is a horse.

* * * * *